(12) United States Patent
Adra

(10) Patent No.: US 7,795,217 B2
(45) Date of Patent: Sep. 14, 2010

(54) METHODS AND COMPOSITIONS FOR CELL-CYCLE REGULATION

(75) Inventor: Chaker N. Adra, 86 E. India Rd., 15 G, Boston, MA (US) 02110

(73) Assignee: Chaker N. Adra, Boston, MA (US)

( * ) Notice: Subject to any disclaimer, the term of this patent is extended or adjusted under 35 U.S.C. 154(b) by 0 days.

(21) Appl. No.: 11/779,381

(22) Filed: Jul. 18, 2007

(65) Prior Publication Data

US 2008/0153749 A1 Jun. 26, 2008

Related U.S. Application Data

(63) Continuation of application No. PCT/US2006/001844, filed on Jan. 18, 2006.

(60) Provisional application No. 60/645,324, filed on Jan. 18, 2005.

(51) Int. Cl.
*A61K 38/00* (2006.01)

(52) U.S. Cl. ............... 514/12; 514/13; 530/326; 530/324; 530/325

(58) Field of Classification Search ............ None
See application file for complete search history.

(56) References Cited

U.S. PATENT DOCUMENTS 5,972,688 A * 10/1999 Lim et al. ............... 435/252.3

FOREIGN PATENT DOCUMENTS

WO WO 98/09992 A2 3/1998
WO 02/062946 * 8/2002

OTHER PUBLICATIONS

Donato et al J. Clinical Investigations vol. 109 p. 51 (2002).*
Jain (Sci. Am., 1994, 271:58-65).*
Gura (Science, 1997, 278:1041-1042).*
Dermer (Bio/Technology, 1994, 12:320).*
Freshney (Culture of Animal Cells, A Manual of Basic Technique, Alan R. Liss, Inc., 1983, New York, p. 4).*
Chinami et al., Binding of HTm4 to cyclin-dependent kinase (Cdk)-associated phosphatase (KAP).Cdk2.cyclin A complex enhances the phosphatase activity of KAP, dissociates cyclin A, and facilitates KAP dephosphorylation of Cdk2. J Biol Chem. Apr. 29, 2005;280(17):17235-42. Epub Jan. 24, 2005.
Li et al., [Regulatory role of HTm4 gene in hematopoietic cell cycle]. Sheng Li Xue Bao. Apr. 25, 2005;57(2):188-92. Chinese. Database BIOSIS Abstract Accession No. PREV200510075039, Y-Abstract.
Nakajima et al., Identification of granulocyte subtype-selective receptors and ion channels by using a high-density oligonucleotide probe array. J Allergy Clin Immunol. Mar. 2004;113(3):528-35.
European Examination Report mailed Dec. 21, 2009 in connection with European Application No. 06718852.4.

* cited by examiner

*Primary Examiner*—Sheela J Huff

(57) ABSTRACT

In some aspects, the invention provides methods and compositions including HTm4, an HTm4 activator, and/or an HTm4 variant to potentiate a KAP phosphatase activity and or inhibit a CDK2 kinase activity. In some embodiments, a functional C-terminal fragment of HTm4 is provided. In other aspects, the invention provides methods and compositions including an HTm4 inhibitor to inactivate or decrease the activation of a KAP phospatase activity and/or activate or relieve the inhibition on a CDK2 kinase activity. Certain aspects of the invention relate to therapeutic compositions and methods for either inhibiting or promoting cell proliferation.

8 Claims, 10 Drawing Sheets b a

Figure 10 a)

SEQ ID NO:5

```
  1 mashevdnae lgsasahgtp gseagpeeln tsvyqpidgs pdyqkaklqv lgaiqilnaa
 61 milalgvflg slqypyhfqk hfffftfytg ypiwgavffc ssgtlsvvag ikptrtwiqn
121 sfgmniasat ialvgtafls lniavniqsl rschsssesp dlcnymgsis ngmvslllil
181 tllelcvtis tiamwcnanc cnsreeissp pnsv
``` b)

SEQ ID NO:6

MKPEETGGSVYQPLDESRHVQRGVLQALGAIQILNGILILALGIFLVCLQHVSHHFRHFFFF
TFYTGYPLWGAVFFISSGSLTVAAGRNPTRMLMQNSFGINIASTTIAFVGTVFLSVHLAFNT
QAFKGCQSSPSPDVCISLGSSSDGLVSLMLILTLLELSVTISISAMWCLGNVCGLREAITSP
PNSVESGILPEGSDSENLNTQPQASEE

SEQUENCE LISTING

```
<160> NUMBER OF SEQ ID NOS: 11

<210> SEQ ID NO 1
<211> LENGTH: 60
<212> TYPE: DNA
<213> ORGANISM: Artificial Sequence
<220> FEATURE:
<223> OTHER INFORMATION: Synthetic Primer

<400> SEQUENCE: 1
cgcggatccg gctctggatc tggatctggt atcgagggaa ggatggcctc ccacgaagtt      60

<210> SEQ ID NO 2
<211> LENGTH: 30
<212> TYPE: DNA
<213> ORGANISM: Artificial Sequence
<220> FEATURE:
<223> OTHER INFORMATION: Synthetic Primer

<400> SEQUENCE: 2
gcactgcagt tattgattac acagaattgg                                       30

<210> SEQ ID NO 3
<211> LENGTH: 19
<212> TYPE: PRT
<213> ORGANISM: Artificial Sequence
<220> FEATURE:
<223> OTHER INFORMATION: Synthetic HTm4 C-terminal Peptide

<400> SEQUENCE: 3

Cys Asn Ala Asn Cys Cys Asn Ser Arg Glu Glu Ile Ser Ser Pro Pro
1               5                   10                  15

Asn Ser Val

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Phosphorylated

<400> SEQUENCE: 4

Lys Arg Thr Ile Arg Arg
1               5
```

<210> SEQ ID NO 5
<211> LENGTH: 214
<212> TYPE: PRT
<213> ORGANISM: Homo sapiens

<400> SEQUENCE: 5

```
Met Ala Ser His Glu Val Asp Asn Ala Glu Leu Gly Ser Ala Ser Ala
1               5                   10                  15

His Gly Thr Pro Gly Ser Glu Ala Gly Pro Glu Leu Asn Thr Ser
            20                  25                  30

Val Tyr Gln Pro Ile Asp Gly Ser Pro Asp Tyr Gln Lys Ala Lys Leu
        35                  40                  45

Gln Val Leu Gly Ala Ile Gln Ile Leu Asn Ala Ala Met Ile Leu Ala
    50                  55                  60

Leu Gly Val Phe Leu Gly Ser Leu Gln Tyr Pro Tyr His Phe Gln Lys
65                  70                  75                  80

His Phe Phe Phe Phe Thr Phe Tyr Thr Gly Tyr Pro Ile Trp Gly Ala
                85                  90                  95

Val Phe Phe Cys Ser Ser Gly Thr Leu Ser Val Val Ala Gly Ile Lys
                100                 105                 110

Pro Thr Arg Thr Trp Ile Gln Asn Ser Phe Gly Met Asn Ile Ala Ser
            115                 120                 125

Ala Thr Ile Ala Leu Val Gly Thr Ala Phe Leu Ser Leu Asn Ile Ala
        130                 135                 140

Val Asn Ile Gln Ser Leu Arg Ser Cys His Ser Ser Glu Ser Pro
145                 150                 155                 160

Asp Leu Cys Asn Tyr Met Gly Ser Ile Ser Asn Gly Met Val Ser Leu
                165                 170                 175

Leu Leu Ile Leu Thr Leu Leu Glu Leu Cys Val Thr Ile Ser Thr Ile
            180                 185                 190

Ala Met Trp Cys Asn Ala Asn Cys Cys Asn Ser Arg Glu Glu Ile Ser
            195                 200                 205

Ser Pro Pro Asn Ser Val
            210
```

<210> SEQ ID NO 6
<211> LENGTH: 213
<212> TYPE: PRT
<213> ORGANISM: Mus musculus

<400> SEQUENCE: 6

```
Met Lys Pro Glu Glu Thr Gly Gly Ser Val Tyr Gln Pro Leu Asp Glu
1               5                   10                  15

Ser Arg His Val Gln Arg Gly Val Leu Gln Ala Leu Gly Ala Ile Gln
            20                  25                  30

Ile Leu Asn Gly Ile Leu Ile Leu Ala Leu Gly Ile Phe Leu Val Cys
        35                  40                  45

Leu Gln His Val Ser His His Phe Arg His Phe Phe Phe Thr Phe
    50                  55                  60

Tyr Thr Gly Tyr Pro Leu Trp Gly Ala Val Phe Phe Ile Ser Ser Gly
65                  70                  75                  80

Ser Leu Thr Val Ala Ala Gly Arg Asn Pro Thr Arg Met Leu Met Gln
                85                  90                  95

Asn Ser Phe Gly Ile Asn Ile Ala Ser Thr Thr Ile Ala Phe Val Gly
                100                 105                 110
```

```
Thr Val Phe Leu Ser Val His Leu Ala Phe Asn Thr Gln Ala Phe Lys
            115                 120                 125

Gly Cys Gln Ser Ser Pro Ser Pro Asp Val Cys Ile Ser Leu Gly Ser
130                 135                 140

Ser Ser Asp Gly Leu Val Ser Leu Met Leu Ile Leu Thr Leu Leu Glu
145                 150                 155                 160

Leu Ser Val Thr Ile Ser Ile Ser Ala Met Trp Cys Leu Gly Asn Val
                165                 170                 175

Cys Gly Leu Arg Glu Ala Ile Thr Ser Pro Pro Asn Ser Val Glu Ser
            180                 185                 190

Gly Ile Leu Pro Glu Gly Ser Asp Ser Glu Asn Leu Asn Thr Gln Pro
        195                 200                 205

Gln Ala Ser Glu Glu
        210

<210> SEQ ID NO 7
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 7

Ala Ile Lys Leu Ala Asp Phe Gly Leu Ala Arg Ala Phe Gly Val Pro
1               5                   10                  15

Val Arg Thr Tyr Thr His Glu Val Val Thr Leu Trp Tyr Arg Ala Pro
                20                  25                  30

Glu Ile Leu Leu
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 8

Ala Ile Lys Leu Ala Asp Phe Gly Leu Ala Arg Ala Phe Gly Val Pro
1               5                   10                  15

Leu Arg Thr Tyr Thr His Glu Val Val Thr Leu Trp Tyr Arg Ala Pro
                20                  25                  30

Glu Ile Leu Leu
        35

<210> SEQ ID NO 9
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 9

Glu Leu Lys Leu Ala Asp Phe Gly Leu Ala Arg Ala Phe Gly Ile Pro
1               5                   10                  15

Val Arg Cys Tyr Ser Ala Glu Val Val Thr Leu Trp Tyr Arg Pro Pro
                20                  25                  30

Asp Val Leu Phe
        35
```

```
<210> SEQ ID NO 10
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 10

Thr Val Lys Leu Ala Asp Phe Gly Leu Ala Arg Ile Tyr Ser Tyr Gln
1               5                   10                  15

Met Ala Leu Thr Pro Val Val Val Thr Leu Trp Tyr Arg Ala Pro Glu
            20                  25                  30

Val Leu Leu
        35

<210> SEQ ID NO 11
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 11

Gln Ile Lys Leu Ala Asp Phe Gly Leu Ala Arg Ile Tyr Ser Phe Gln
1               5                   10                  15

Met Ala Leu Thr Ser Val Val Val Thr Leu Trp Tyr Arg Ala Pro Glu
            20                  25                  30

Val Leu Leu
        35
```

METHODS AND COMPOSITIONS FOR CELL-CYCLE REGULATION

RELATED APPLICATIONS

This application is a continuation of PCT/US2006/001844 filed Jan. 18, 2006, which was published under PCT Article 21(2) in English, and also claims the benefit under 35 U.S.C. 119(e) of U.S. Provisional Application No. 60/645,324, filed Jan. 18, 2005, the disclosures of which are incorporated herein by reference.

FEDERALLY SPONSORED RESEARCH

This invention was made with Government support under the National Institute of Allergy and Infectious Diseases Grant No.: NIH Grant AI 43663 and from the American Cancer Society under Grant No.: RSG-01-241-01-LIB. The Government may have certain rights to this invention.

BACKGROUND

HTm4 (MS4A3) is the third member of subfamily A in an extensive membrane-spanning four-domain gene family. These genes are only loosely related at the sequence level, but their encoded proteins share a common four-transmembrane topology, including CD20 (MS4A1) and FcεRI (MS4A2). To date, few functions for the MS4 family of proteins have been ascribed. However, a diverse functionality is beginning to emerge. These functions include roles such as cell surface signaling receptors and intracellular adapter proteins.

SUMMARY AND DESCRIPTION OF THE INVENTION

The invention relates to methods and compositions for regulating cell-cycle progression.

In one aspect, embodiments of the invention relate to methods and compositions for slowing, inhibiting, or arresting cell cycle progression. For example, certain embodiments of the invention relate to killing cells (e.g., tumor cells, cancer cells, or other diseased cells) or inducing apoptosis in cells. In another aspect, embodiments of the invention relate to promoting cell growth, development, and/or replication (e.g., promoting cell cycle progression. For example, certain embodiments of the invention relate to promoting growth or development of cells that are quiescent or that have stopped growing. In some embodiments, methods and compositions of the invention may be used to delay or reverse premature cell cycle arrest or cell death. Accordingly, aspects of the invention relate to treating one or more degenerative diseases (e.g., neuro-degenerative diseases). Aspects of the invention may be practiced in vitro or ex vivo or in experimental systems. Other aspects of the invention relate to therapeutic compositions and methods for treating patients (e.g., human patients).

Aspects of the invention relate to using HTm4 (e.g., overexpressing or up-regulating HTm4) or variants or agonists thereof to inhibit CDK2. CDK2 is an important regulator of cell cycle progression. Inactivating or inhibiting CDK2 is useful to arrest cell cycle progression, particularly at the early stages of a cell cycle. According to the invention, inactivation of CDK2 may be useful for selectively killing cancer cells (e.g., via apoptosis). In some embodiments, methods of the invention relate to using fragments of HTm4 (e.g., one or more C-terminal fragments of HTm4), or variants thereof, to inhibit CDK2 activity, potentiate KAP phosphatase activity, or a combination thereof.

Accordingly, aspects of the invention including killing cancer or tumor cells using HTm4 or variants or agonists thereof. Other aspects of the invention relate to potentiating or activating KAP phosphatase activity. Yet further aspects of the invention relate to methods for excluding or reducing cyclin A interaction with CDK2.

Other aspects of the invention relate to using antagonists of HTm4 to activate CDK2, inactivate (or at least not potentiate) KAP phosphatase activity, or a combination thereof.

One aspect of the invention relates to HTm4 activators (e.g., compounds that increase the expression, translation and/or function of) of HTm4. One aspect of the invention relates to the HTm4 polypeptide or functional variants thereof (e.g., species variants, sequence variants, deletion variants, HTm4 fragments, and sequence variants thereof). One aspect of the invention relates to nucleic acids encoding HTm4 polypeptides or functional variants thereof (e.g., species variants, sequence variants, deletion variants, HTm4 fragments, and sequence variants thereof). Another aspect of the invention relates to inhibitors of HTm4 (e.g., compounds that decrease the expression, translation and/or function of) of HTm4. In some embodiments, inhibitors may be antibodies to HTm4 or variants thereof (e.g., species variants, sequence variants, deletion variants, HTm4 fragments, and sequence variants thereof). In certain embodiments, an inhibitor may be an antibody (or other binding moiety such as a nucleic acid aptamer) that specifically binds to one or more epitopes of HTm4 (e.g., human HTm4 or mouse HTm4). The epitope(s) may be one or more C-terminal epitopes.

According to aspects of the invention, HTm4 acts as an inhibitor of CDK2 interaction with cyclin A, and an activator of KAP. Accordingly, HTm4 also inhibits CKD2 by activating KAP. Accordingly, aspects of the invention also relate to activating KAP (e.g., by increasing the activity of and/or increasing the expression, translation and/or intracellular amount of HTm4, or by providing a variant thereof such as an HTm4 sequence variant or fragment). However, other aspects of the invention relate to inhibiting KAP (e.g., by decreasing the activity of and/or decreasing the expression, translation and/or intracellular amount of HTm4). Accordingly, aspects of the invention include increasing or inhibiting the interaction between HTm4 and KAP. An important activity of KAP is the KAP phosphatase activity. Accordingly, methods of activating or inhibiting KAP include methods of activating or inhibiting, respectively, the KAP phosphatase activity.

Aspects of the invention relate to blocking CDK2 (e.g., by activating the KAP phosphatase activity) to block cell cycle progression and/or to induce apoptosis. Accordingly, aspects of the invention are useful to selectively kill cells (e.g., to kill cancer cells).

Aspects of the invention relate to influencing (e.g., increasing or decreasing the activity and/or amount of) HTm4, KAP, and/or CDK2 (e.g., to promote apoptosis in cancer cells, or to prevent apoptosis in other cells).

Aspects of the invention include methods and compositions for synchronizing cells (e.g., by synchronizing their cell cycles) in vivo or in vitro. Other aspects of the invention include methods and compositions for identifying or screening therapeutic compounds (or candidate compounds) by identifying compounds that interact with HTm4 (or a sequence variant or fragment, e.g., C-terminal fragment) and either activate or inactivate its function. The function of HTm4 may be assayed as described herein (e.g., in an assay described herein wherein the effect of HTm4 on CDK2 and/or KAP activity is assayed, or a variant of the assay wherein the compound being tested is provided along with HTm4 in a format that allows for the competitive effects of HTm4 and the compound to be assayed). It should be appreciated that any of the methods or compositions described herein in the context of HTm4 also may be practiced using a sequence variant or fragment of HTm4 (e.g, a C-terminal fragment of HTm4). Accordingly, aspects of the invention include methods for identifying binding agents, antagonists, activators, and/or inhibitors that are useful for controlling cell-cycle progression. Accordingly, the invention includes designing, discovering, making, and/or screening new or existing molecules (including small molecules, nucleic acids, peptides, aptamers, etc.).

Aspects of the invention include compositions and methods for treating cancer and or other forms of uncontrolled cell growth by administering a therapeutically effective amount of an HTm4 composition or an HTm4 activator composition of the invention. Other aspects of the invention include compositions and methods for promoting, retaining, or stimulating cell growth by administering a therapeutically effective amount of an HTm4 inhibitor composition of the invention.

The invention includes formulations and/or preparations that are pharmaceutically and/or physiologically acceptable, including sterilized formulations and/or preparations. The invention includes methods for treating disease (e.g., cancer) in vertebrates, including in mammals, including in humans.

Other aspects of the invention include combinations of HTm4 compounds, HTm4 activators, or HTm4 inhibitors with one or more other therapeutic compounds. Aspects of the invention also may include activating (e.g., administering, increasing the expression of) or inactivating (e.g., deleting, decreasing the expression and/or translation of, inhibiting the function of) p21 and/or p53.

Aspects of the invention also include kits. According to the invention kits may include any one or more of the compositions or pharmaceutical preparations described herein (including antibodies and aptamers that may act as activators or inhibitors of the activities descried herein).

BRIEF DESCRIPTION OF THE DRAWINGS

FIG. 10. a, Amino acid sequence of human HTm4 (MS4A3, accession number: Q96HJ5). b, Amino acid sequence of mouse HTm4 (accession number: Q920C4).

BRIEF DESCRIPTION OF THE SEQUENCES

Figure 1:
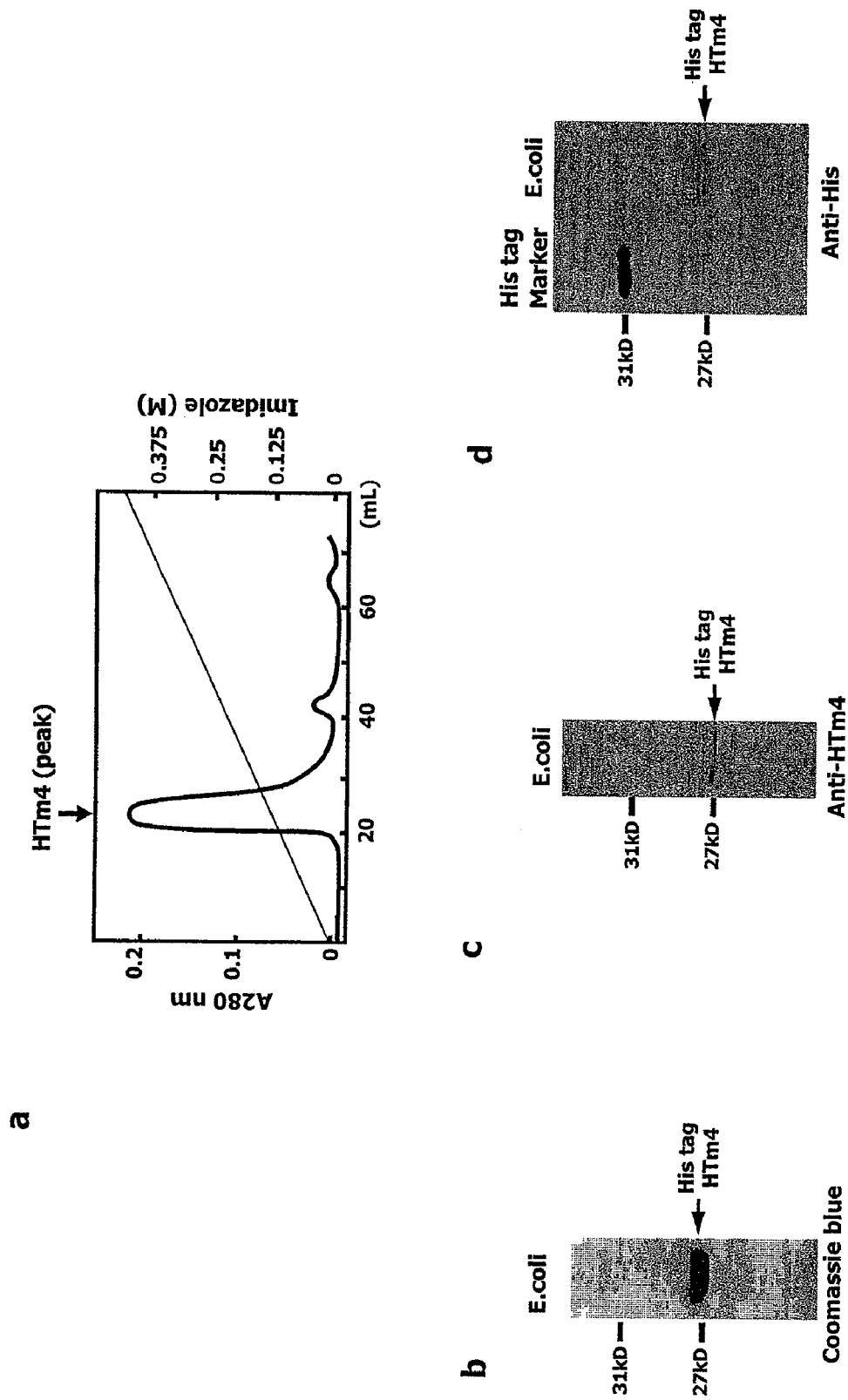
FIG. 1. Purification and characterization of HTm4. a, elution of His-HTm4 from a nickel column. b, Coomassie Blue staining of the eluted peak corresponding to HTm4. c, Western blot analysis of HTm4 fraction of E. coli lysate using an anti-HTm4 antibody. d, Western analysis of HTm4 fraction of E. coli lysate using anti-His tag antibody.

SEQ ID NO: 1—Nucleotide sequence for forward primer hHTm4BamH1. 5'-cgc-gga-tcc-ggc-tct-gga-tct-gga-tct-ggt-atc-gag-gga-agg-atg-gcc-tcc-cac-gaa-gtt-3'

SEQ ID NO:2—Nucleotide sequence for reverse primer hHTm4Pst1. 5'-gca-ctg-cag-tta-ttg-att-aca-cag-aat-tgg-3'

SEQ ID NO:3—Amino acid sequence of HTm4 C-terminal peptide CNANCCNSREEISSPPNSV

SEQ ID NO:4—Amino acid sequence of peptide K-R-pT-I-R-R. p=phosphorylated

SEQ ID NO:5—Amino acid sequence of human HTm4 (accession number: Q96HJ5).

SEQ ID NO:6—Amino acid sequence of mouse HTm4 (accession number: Q920C4).

DETAILED DESCRIPTION

Cell cycle progression is regulated by the sequential activation, and inactivation, of the cyclin-dependent kinases (cdks). Cdks, themselves, are substrates for regulatory phosphorylation and dephosphorylation. The phosphorylation status of cdks is controlled by a discrete class of regulatory kinases and phosphatases. Cdk activity is controlled by activatory and inhibitory proteins, the latter exemplified by p21 and p27. Binding of inhibitors such as p21 and p27 to different cyclin.cdk complexes is sufficient to arrest the cell cycle. Conversely, inactive, monomeric cdk can be activated via association with a specific cyclin and the concurrent phosphorylation of a conserved and essential threonine residue, such as threonine 160 (Thr$^{160}$) in cdk2, which is located within the activation segment (T-loop) of the kinase.

In addition to cyclin association, full activation of cdk2 requires phosphorylation of Thr$^{160}$ and dephosphorylation of Thr$^{14}$ and Tyr$^{15}$. Thr$^{160}$ of cdk2 is phosphorylated by CAK (cdk-associated kinase), whereas its dephosphorylation is critical for inactivation. This dephosphorylation is executed by a serine/threonine-directed phosphatase, KAP. According to aspects of the invention, exogenous expression of KAP slows the G$_1$ phase cell cycle progression in HeLa cells and that aberrant KAP transcripts are detected in some hepatocellular carcinomas. According to aspects of the invention, KAP has the same biological effects as cdk inhibitors, although their modes of actions may be different. KAP can bind to cdk2 either in the presence or absence of cyclins. However, KAP can only dephosphorylate cdk2 when cyclin A is degraded or disassociated, in a mechanism that may control access of KAP to its substrate Thr$^{160}$. Cyclin binding may therefore control access of KAP to its substrate phosphothreonine 160. According to aspects of the invention, HTm4 interacts directly with the KAP via its C terminus and exogenous expression of HTm4 leads to dephosphorylation of cdk2 and cell cycle arrest at the $G_0/G_1$ phase. In further aspects of the invention, the presence of HTm4 in the KAP.cdk2.cyclin A complex controls cdk2 activity in a dual fashion. First, HTm4 binding causes exclusion of cyclin A from its interaction with cdk2. Second, HTm4 binding potentiates KAP enzymatic activity and causes conformational changes that regulate access to Thr$^{160}$. According to aspects of the invention, the discovery that HTm4 (and a C-terminal fragment of HTm4) may interact directly with KAP and/or CDK2 without requiring any additional intracellular factor(s) or molecule(s) provides new experimental and therapeutic compositions and methods as described herein.

Aspects of the invention relate to methods of slowing, inhibiting, and/or arresting cell cycle progression by providing an HTm4 activator. An activator may be a composition capable of interacting with HTm4 and promoting its interaction with CDK2 and/or KAP. An activator may be a composition that increases the expression (e.g., transcription and/or translation) of endogenous HTm4. Other aspects of the invention relate to methods of slowing, inhibiting, and/or arresting cell cycle progression by providing exogenous HTm4 or a variant thereof (for example a species variant, a functional sequence variant, a functional fragment or functional variant thereof) in an amount sufficient to inhibit CDK2 and/or activate KAP. In one embodiment, up-regulation of HTm4 expression causes arrest of the cell cycle. An inhibitor of CDK2 or activator of KAP may be a fragment of HTm4 or full-length HTm4. A fragment of HTm4 may be a portion of HTm4 capable of retaining the function of HTm4. A fragment of HTm4 can be of any length. In certain embodiments, a fragment of HTm4 may be a C-terminal fragment of HTm4. A fragment (e.g., a C-terminal fragment) of HTm4 may be 10, 15, 20, 21, 22, 23, 24, 25, 26, 27, 28, 29, 30, 35, 40, 45, 50, 55, 60, 65, 70, 75, 80, 85, 90, 95, or 100 amino acids in length. However, longer or shorter fragments also may be used. In some embodiments, a C-terminal fragment includes amino acids in the C-terminal region of HTm4, but not the C-terminal-most amino acids (e.g., not the last 1, 2, 3, 4, or 5 amino acids). In some embodiments, a C-terminal fragment of HTm4 includes the C-terminal 22 amino acids of human or mouse HTm4. In some embodiments, a C-terminal fragment of HTm4 consists of the C-terminal 22 amino acids of human or mouse HTm4. In some embodiments, a C-terminal fragment of HTm4 includes the C-terminal 19 amino acids of human or mouse HTm4. In some embodiments, a C-terminal fragment of HTm4 consists of the C-terminal 19 amino acids of human or mouse HTm4. In some embodiments, a C-terminal fragment shown in SEQ ID NO: 3 may be used. It should be appreciated that HTm4 (or one or more fragments, e.g., C-terminal fragments thereof) from one or more other species (e.g, one or more animal species, on or more other mammals such as rat, pig, monkey, other primate, etc.) may be used in aspects of the invention. Functional variants of any of the HTm4 peptides described herein also may be used. Useful HTm4 sequence variants may include one or more (e.g., 1, 2, 3, 4, 5, 6, 7, 8, 9, 10 or more) amino acid changes relative to a natural sequence (e.g., relative to the human or mouse sequence provided in SEQ ID NOs. 5 and 6, respectively). Amino acid changes may be conservative amino acid changes. In some embodiments, a sequence variant of an HTm4 C-terminal fragment (e.g., a human or mouse C-terminal fragment) may be used. In certain embodiments, a variant of SEQ ID NO: 3 may be used. In certain embodiments, a sequence variant of SEQ ID NO: 3 may include between 1 and 5 (e.g, 1, 2, 3, 4, or 5) conservative amino acid changes. In certain embodiments, a variant including (e.g., consisting of, or consisting essentially of) a portion of the peptide shown in SEQ ID NO: 3 may be used. For example, a peptide lacking one or more (e.g., 1, 2, 3, 4, or 5) of the N-terminal and/or or C-terminal amino acids of SEQ ID NO: 3 may be used. In some embodiments a peptide dimer or multimer may be used (e.g., a dimer of a peptide including the sequence of SEQ ID NO: 3). A functional dimer may include a synthetic spacer or other linker linking the individual monomer peptides (e.g., via their N-terminal ends). The function of any HTm4 variant described herein may be evaluated using any suitable assay(s) including one or more of the assays provided herein.

It should be appreciated that HTm4 or a variant thereof may be provided exogenously in the form of a peptide or in the form of a nucleic acid that expresses the HTm4 or variant thereof.

Other aspects of the invention relate to methods of up-regulating or increasing cell cycle progression by providing an HTm4 inhibitor. An inhibitor may be a composition capable of interacting with HTm4 to inhibit its function (e.g., to relieve CDK2 inhibition and/or decrease KAP potentiation). In other embodiments, an HTm4 inhibitor may be a compound that decreases (e.g., partially or completely) HTm4 expression. Accordingly, an inhibitor may be an antibody, an antibody fragment, an aptamer, another specific binding moiety, siRNA, microRNA, another small molecule, etc., or any combination thereof. A binding moiety (e.g., an antibody or antibody fragment) may bind specifically or selectively (e.g., with high binding affinity) to HTm4 or a variant thereof described herein. In certain embodiments, an antibody (e.g., a monoclonal or polyclonal antibody) that is specific or selective for (e.g., has high binding affinity for) HTm4 or a variant thereof may be obtained. In some embodiments an antibody that binds specifically or selectively to a C-terminal fragment (e.g., a fragment having a sequence of SEQ ID NO. 3) may be used. A useful antibody may be raised against a C-terminal HTm4 fragment (e.g., a fragment having a sequence of SEQ ID NO: 3) or an epitope thereof.

In some embodiments, a composition of the invention (e.g., HTm4, a variant of HTm4, an HTm4 activator, or an HTm4 inhibitor such as an antibody or other binding agent) may include a peptide tag sequence (e.g., an antigen or other tag that is useful for purification). In some embodiments, a composition of the invention may include one or more targeting moieties (e.g., a targeting peptide) to target the composition to one or more cell types and/or to help the composition enter a cell through a cell membrane and/or to target the composition to a sub-cellular location (e.g., the nucleus).

In certain embodiments, an inhibitor is an antibody fragment. As is well known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of an antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody.

An isolated F(ab')₂ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')₂ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

In certain embodiments, an antibody or antibody fragment is a monoclonal antibody or antibody. In other embodiments, an antibody or antibody fragment is a polyclonal antibody or antibody fragment. In some embodiments, the Fc portions of an antibody may be replaced so as to produce different antibody isotypes, such as IgM, IgG, or IgA antibodies or antibody fragments.

In aspects of the invention, an antibody or antibody fragment is a human antibody or antibody fragment. In certain embodiments, an antibody or antibody fragment is a humanized antibody or antibody fragment.

In certain embodiments, compositions of the invention may be isolated. As used herein, the term "isolated" means that the compositions are substantially pure and are essentially free of other substances with which they may be found in nature or in vivo systems to an extent practical and appropriate for their intended use. In particular, the compositions are sufficiently pure and are sufficiently free from other biological constituents of their hosts cells so as to be useful in, for example, producing pharmaceutical preparations or sequencing. Because an isolated composition of the invention may be admixed with a pharmaceutically acceptable carrier in a pharmaceutical preparation, the composition may comprise only a small percentage by weight of the preparation. The composition is nonetheless substantially pure in that it has been substantially separated from the substances with which it may be associated in living systems.

In certain embodiments, compositions of the invention may be provided in combination (e.g., mixed with) or in a kit along with one or more other HTm4 compositions (e.g., HTm4, one or more functionally equivalent variants of HTm4, a nucleic acid encoding HTm4 or one or more functionally equivalent variants thereof), HTm4 activators, HTm4 inhibitors, CDK2 activators, CDK2 inhibitors, KAP activators, and/or KAP inhibitors. In certain embodiments, a composition of the invention may be provided in a pharmaceutically-acceptable preparation (along with one or more pharmaceutically-acceptable salts). In certain embodiments, a composition of the invention may be sterilized. In some embodiments, a composition of the invention may be provided along with one or more carrier or other molecule(s) described herein that may confer a beneficial property on the composition. Examples of beneficial molecules include those that increase the stability of a composition, those that increase the bioavailability of a composition, those that increase the functional properties (e.g., in vitro or in vivo properties) of a composition, etc., or any combination thereof.

A "functionally equivalent variant" is a compound having the same function (i.e., the ability to interact with HTm4) as the compositions of the invention. A functionally equivalent variant may be peptide in nature but it is not so limited. For example, it may be a carbohydrate, a peptidomimetic, etc.

As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M, I, L, V; (2) F, Y, W; (3) K, R, H; (4) A, G; (5) S, T; (6) Q, N; and, (7) E, D.

Functional equivalent variants can have identity to the compositions explicitly recited herein. That is, such variants may have at least 99% identity, at least 98% identity, at least 97% identity, at least 96% identity, at least 95% identity, at least 94% identity, at least 93% identity, at least 92% identity, at least 91% identity, at least 90% identity, at least 85% identity, at least 80% identity, at least 75% identity, at least 70% identity, at least 65% identity, at least 60% identity, at least 55% identity, at least 50% identity, at least 45% identity, at least 40% identity, at least 35% identity, at least 30% identity, at least 25% identity, at least 20% identity, at least 10% identity, or at least 5% identity to the amino acid sequences provided herein.

Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the particular CDR. These and other methods for making substitutions will be known to those of ordinary skill in the art and may be found in references which compile such methods, e.g. Sambrook or Ausubel. As used herein, the terms "functional variant", "functionally equivalent variant" and "functionally active variant" are used interchangeably.

In some aspects of the invention, a composition may be modified. Modifications embrace fusion proteins comprising all or part of a HTm4 amino acid sequence. The invention thus embraces fusion proteins comprising full length HTm4 or fragments thereof and endosomal targeting signals such as the human invariant chain (Ii). An "endosomal targeting portion" of the human invariant chain or other targeting polypeptide is that portion of the molecule which, when fused or conjugated to a second polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule.

The compositions of the invention may be delivered to the cell, in vitro or in vivo, either alone or with a carrier. For instance, colloidal dispersion systems may be used to deliver a composition. As used herein, a "colloidal dispersion system" refers to a natural or synthetic molecule, other than those derived from bacteriological or viral sources, capable of delivering to and releasing the composition. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 ÿ can encapsulate large macromolecules within the aqueous interior and these macromolecules can be delivered to cells in a biologically active form (Fraley, et al., *Trends Biochem. Sci.,* 6:77 (1981)).

Polymeric delivery systems also have been used successfully to deliver compositions into cells, as is known by those skilled in the art. Lipid formulations for such delivery are commercially available from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235-241 (1985), which is hereby incorporated by reference.

In some aspects of the invention, a signal molecule may be attached to a composition of the invention to aid in delivery to a cell. One or more signal molecules may be attached to a composition. A signal molecule or signal peptide may be a short (e.g., 15-60 amino acids long) peptide chain that directs the post translational transport of a protein. Some signal peptides are cleaved from the protein by enzymes such as signal peptidase after the protein is transported. The amino acid sequence of a signal peptide directs a protein to a certain organelle, such as the nucleus, mitochondrial matrix and endoplasmic reticulum. In certain embodiments, a signal molecule or signal peptide is a nuclear localization signal (NLS). A nuclear localization signal is a signal peptide that directs a composition to the nucleus. A nuclear localization signal may include positively-charged amino acids. The NLS may be located within the composition. One of ordinary skill in the art would be able to determine such a signal molecule. In certain embodiments, a signal molecule will be such that it does not affect the structure of the composition to which it is attached. A signal molecule or peptide may be attached to either the C-terminus or the N-terminus of a composition. In some embodiments, a signal molecule or peptide may be attached to both the C-terminus or the N-terminus of a composition. The signal molecule or peptide may be the same on both the C- and N-terminus or may be different signal molecules or peptides.

The phrase "pharmaceutically acceptable" is employed herein to refer to those compounds, materials, compositions, agents, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound or agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The term "pharmaceutically-acceptable salts" as used herein refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

It should be appreciated that certain aspects of the invention may be used to treat cancer or other cell-proliferative diseases, whereas other aspects of the invention may be used to promote cell growth for example to treat diseases associated with cell death or lack of cell growth (e.g., diabetes, degenerative conditions, neurodegenerative conditions, neuromuscular degenerative conditions, etc.). In particular aspects of the invention may be used to treat diseases associated with cell cycle disorder (either over-proliferation such as cancer, or proliferation deficiencies) associated with blood or blood cells (hematopoietic cells). Aspects of the invention may be particularly useful to selectively treat cancer since cancer cells may under-express HTm4 and/or KAP.

According to the invention, the terms "treat" or "treatment" may include prophylaxis and/or therapy, and may include managing a subject's symptoms or halting the progression of a disease. In other embodiments, treatment may include preventing, slowing, stopping or reversing (e.g. curing) the development of a disease, and/or the onset of certain symptoms associated with a disease in a subject with, or at risk of developing the disease. Accordingly, a therapy may include preventing, slowing, stopping or reversing (e.g. curing) the proliferation of diseased cells (e.g., cancer cells) in a subject. In some aspects, an HTm4 composition of the invention may be cytotoxic. In other aspects, an HTm4 composition of the invention may be cytostatic. In some aspects of the invention, suitable doses and/or amounts of one or more compositions of the invention for in vitro and/or in vivo use (e.g., for therapeutic use) may be determined by one of ordinary skill in the art.

EXAMPLES

Example 1

Materials and Methods

Subcloning, Expression, Purification, and Characterization of HTm4 and KAP

Human HTm4 was reverse transcribed-PCR cloned from total RNA extracted from human peripheral blood mononuclear cells from healthy volunteers with informed consent, using the following 5'- and 3'-primers (forward primer: hHTm4BamH1: 5'-cgc-gga-tcc-ggc-tct-gga-tct-gga-tct-ggt-atc-gag-gga-agg-atg-gcc-tcc-cac-gaa-gtt-3' SEQ ID NO:1; reverse primer: hHTm4Pst1: 5'-gca-ctg-cag-tta-ttg-att-aca-cag-aat-tgg-3' SEQ ID NO:2). The PCR product was subcloned into the pQE-80L vector (Qiagen). An N-terminal His tag was conferred during subcloning.

Recombinant HTm4 was purified from transformed JM109 *Escherichia coli* as follows. Protein production was induced by the addition of isopropyl 1-thio-β-D-galactopyranoside to bacterial liquid culture in logarithmic phase. Bacteria were harvested by centrifugation at 6,000 rpm for 30 min. The bacterial pellet was lysed by sonication on ice (20 KW, 15 min) in 50 ml of N buffer (20 mM Tris-HCl, pH 8.0, containing 0.1 M NaCl, 1 mM phenylmethylsulfonyl fluoride, 1 mM β-mercaptoethanol). The bacterial lysate was centrifuged at $20 \times 10^4$ g at 4° C. for 30 min. The remaining pellet was lysed in 40 ml of N buffer containing 6 M guanidine HCl. Proteins were bound to a 20-ml nickel-chelated Sepharose column (Amersham Biosciences) and were refolded by exposure to a 6-0 M urea gradient at 0.2 ml/min. The refolded protein sample was eluted with a gradient of N buffer containing 0.5 M imidazole and 0.3% deoxycholate. The peak fraction containing HTm4 was collected and purified by XArrest agarose after His tag cleavage with 4 units of Factor Xa (Novagen). Wild-type KAP, inactive KAP (C140S), and mutant KAP were expressed and purified as described previously (Song, H., Hanlon, N., Brown, N. R., Noble, M. E., Johnson, L. N., and Barford, D. (2001) *Mol. Cell.* 7, 615-626).

Western Blotting of HTm4

For the Western blot, 10 µl of purified protein was boiled in SDS sample buffer and resolved by 15% PAGE. After electrotransfer to polyvinylidene difluoride, the membrane (Bio-Rad) was blocked followed by incubation with either anti-His tag antibody diluted at 1:5,000 (MBL) or anti-HTm4 antibody (Zymed Laboratories Inc.) and horseradish peroxidase-conjugated anti-rabbit IgG. Signals were detected using ECL (Amersham Biosciences).

Protein Interaction Analyses (Surface Plasmon Resonance Assay)

The immobilization of proteins to sensor chips (CM-5 chip) was performed using a carbodiimide covalent linkage protocol (Amersham Biosciences). KAP was coupled to the sensor chip at 2,800 resonance units (RU). Nonspecific human immunoglobin was coupled to the surface of the sensor chip (anti-β 2m antibody BBM.1) at 2,900 RU. Protein interaction assays were carried out using the BioSensor Biacore 2000 (Biacore). An HTm4 C-terminal peptide composed of 22 amino acids (CNANCCNSREEISSPPNSV SEQ ID NO:3) was synthesized. Either full-length HTm4 protein (20 µM), or HTm4 C-terminal peptide (1 mM) in 50 mM HEPES containing 1 mM EDTA, 1 mM DTT, 5% glycerol, and 0.1% Tween 20 was examined at a flow rate of 10 µl/min.

Protein Activity Assays

KAP phosphatase activity was examined by the detection of hydrolysis of p-nitrophenyl phosphate (pNPP) (WAKO) as described previously (Song, H., Hanlon, N., Brown, N. R., Noble, M. E., Johnson, L. N., and Barford, D. (2001) *Mol. Cell.* 7, 615-626). The time course of phosphatase activity for KAP was examined. 20 µl of reaction mixture containing 50 mM Tris-HCl, pH 7.5, 0.15 M NaCl, 2 mM DTT, 0.5 mM EDTA, 3 mM pNPP, 40 µM KAP, 4 µM cdk cyclin A (Upstate Biotechnology), and 20 µM HTm4 was incubated at 30° C. for the indicated times. The reaction was halted by the addition of 0.1 M NaOH. The phosphatase activity in 5 µl of each sample was measured as $A_{410}$. To investigate the effect of HTm4 on KAP, KAP phosphatase activity was assessed with different HTm4 concentrations in the presence of pNPP. Reaction velocity was measured in the presence of 0.0025-20 µM HTm4. All reaction mixtures contained 40 µM KAP and 4 µM active cdk2.cyclin A. Activities of either wild-type or C140S (inactive) KAP were examined in the different reaction mixtures, with or without 20 µM HTm4 (C-terminal peptides/nonrelated peptides at 0.1 mM) or 4 µM active cdk.cyclin A (cdk2 monomer).

Kinetic Measurements

To investigate the effect of HTm4 on KAP, the initial reaction velocity of KAP was assessed using different concentrations of active cdk2.cyclin A as the substrate in the presence or absence of HTm4. The results were analyzed further using a Lineweaver-Burk plot.

KAP Dephosphorylation of Peptide or Protein Substrates

KAP dephosphorylation of phosphorylated proteins or peptide substrates was examined using the Ser/Thr Phosphatase Assay Kit 1 (Upstate Biotechnology) according to the manufacturer's instructions. Phosphorylated $Thr^{160}$ of cdk2 and K-R-pT-I-R-R peptide were used as substrates for the assay. Concentrations of KAP and HTm4 were both 20 µM; concentrations of p-cdk2 and peptide substrates (K-R-pT-I-R-R) were 10 and 25 µM, respectively. Reactions were performed in pNPP Ser/Thr Assay Buffer, containing 50 mM Tris-HCl, pH 7.0, and 100 µM $CaCl_2$. To examine the importance of the HTm4 C-terminal region and to confirm the KAP phosphatase activity enhancement effect of HTm4, an HTm4 C-terminal peptide composed of 22 amino acids (CNANC-CNSREEISSPPNSV SEQ ID NO:3) was synthesized. The phosphatase enhancement activity of the HTm4 C-terminal region was examined using the assay protocol described above. All assays were performed in triplicate, with the average values and standard deviations displayed on the plot (see FIGS. 2 and 3).

Circular Dichroism Spectroscopy

Circular Dichroism (CD) spectroscopic measurements were performed on a Jasco J-700 (Jasco, Japan). Spectra measurements were recorded from 250 to 320 nm. The spectra change of KAP was measured by comparing two different KAP samples in the same solution (20 mM Tris-HCl, pH 7.2, 0.15 M NaCl). Sample A contained 5 µM KAP and an excess amount of HTm4 C-peptide (50 µM). The contents of sample B were identical to those in sample A, except for HTm4 C-peptide. The difference in spectra was further converted to parameter (mean residue ellipticity) and plotted on the graph in FIG. 4.

Cyclin A Dissociation Assay

The status of the cdk2.cyclin A complex was examined in the presence and absence of HTm4. Recombinant cdk2.cyclin A (Upstate) and His-tagged KAP were combined in vitro and incubated in the absence or presence of either 1 or 10 µM HTm4. The samples were added to a nickel magnet bead matrix (Toyobo) to capture His-tagged KAP protein and any associated binding partners. The bound fractions were resolved by SDS-PAGE and Western blotted for the presence of cyclin A (Santa Cruz Biotechnology). An alkaline phosphatase conjugated to anti-rabbit IgG (EY Laboratory) was used to visualize the amount of bound cyclin A present in the KAP cdk2 complex. 10 µl of 10 µM cdk2.cyclin A and 10 µl of 10 µM His-tagged KAP were mixed in 20 mM Tris-HCl, pH 7.5, buffer containing 0.15 M NaCl, 1 mM β-mercaptoethanol, and 0.1% Tween 20. After incubating at room temperature for 5 min, either 10 µl of 10 µM HTm4 (without His tag) or its buffer was added to the reaction mixture. After incubating at room temperature for 5 min, 5 µl of nickel magnet beads was added to each mixture. The fractions bound to His-tagged KAP were washed with the reaction buffer and boiled for SDS-PAGE. The gel was stained with a silver staining kit (ATTO).

Example 2

Direct Binding of KAP and HTm4 in Vitro

HTm4 and KAP phosphatase may be coimmunoprecipitated from hematopoietic cells. This example determines whether the interaction between HTm4 and KAP is direct or if it involves an intermediary protein. A purified protein-protein interaction system can be used to determine whether HTm4 and KAP interact directly.

His-tagged HTm4 was produced in E. coli and purified by fast protein liquid chromatography (FIG. 1a). The eluted peak corresponding to HTm4 was visualized by Coomassie Blue staining (FIG. 1b) and then analyzed by Western blot. Both anti-HTm4 and anti-His antibodies detected a 27-kDa band corresponding to HTm4 (FIG. 1, c and d).

FIG. 1 shows the elution of His-HTm4 from a nickel column. His-tagged HTm4 was expressed in E. coli, refolded with the column methods described, and eluted with a gradient concentration of 0.5 M imidazole. The eluted peak corresponding to HTm4 was visualized by Coomassie Blue staining. Western blot analysis of HTm4 fraction of E. coli lysate was performed. The HTm4-containing fraction was confirmed by Western blot using an anti-HTm4 antibody. The HTm4-containing fraction was confirmed by Western blot with anti-His tag antibody.

Surface plasmon resonance was used to detect direct binding of purified HTm4 to KAP. Full-length KAP protein was coupled to a sensor chip CM-5 shell (Amersham Biosciences). Compared with either uncoupled or nonspecifically coupled chips (coupled to anti-β 2m antibody BBM.1), an immediate increase in mass was observed when either full-length HTm4 (FIG. 2a) or a C-terminal peptide from HTm4 (FIG. 2b) was passed over KAP-coupled sensor chips.

Figure 2:
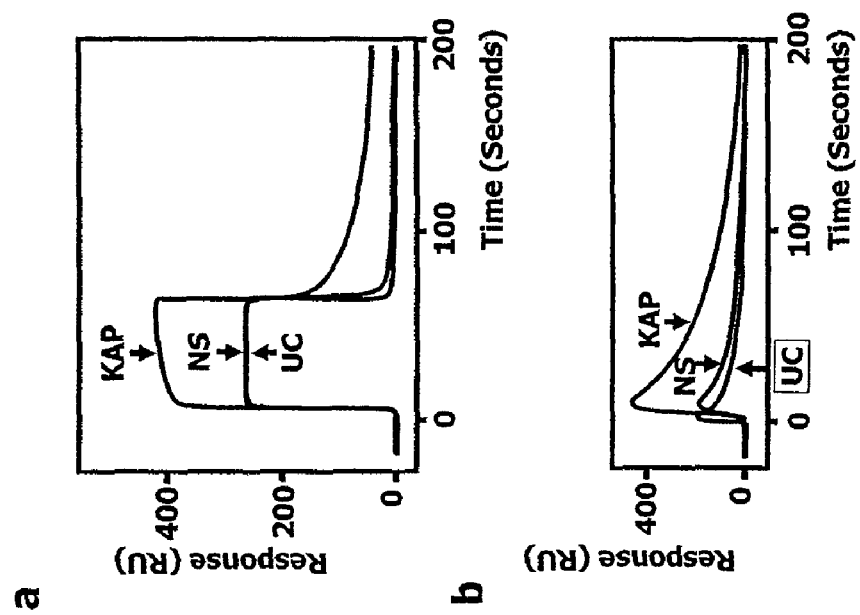
FIG. 2. KAP and HTm4 interaction by BioSensor analysis. a, Graph showing binding of full-length HTm4 protein to KAP. b, Graph showing binding of HTm4 C-terminal to KAP.

FIG. 2 shows KAP and HTm4 interaction by BioSensor analysis. Binding of full-length HTm4 protein to KAP was demonstrated. The interactions of HTm4 with immobilized proteins were analyzed on a sensor chip (CM-5) cell. KAP was coupled to the surface of the sensor chip at 2,800 RU; nonspecific human immunoglobulin (NS) was coupled to the surface of the sensor chip (anti-β2m antibody BBM.1) at 2,900 RU; UC, uncoupled sensor chip. Binding of 20 µM full-length HTm4 protein in 50 mM HEPES containing 1 mM EDTA, 1 mM DTT, 5% glycerol, and 0.1% Tween 20 was examined at a flow rate of 10 µl/min. Binding of HTm4 C-terminal to KAP was demonstrated. The interactions of HTm4 with immobilized proteins were analyzed on a sensor chip (CM-5) cell. KAP was coupled to the surface of the sensor chip at 2,800 RU; nonspecific human immunoglobulin was coupled on the surface of the sensor chip (anti-β 2m antibody BBM.1) at 2,900 RU. Binding of 1 mM HTm4 C-terminal peptide in 50 mM HEPES containing 1 mM EDTA, 1 mM DTT, 5% glycerol, and 0.1% Tween 20 was examined at a flow rate of 10 µl/min. Responses from uncoupled cells were subtracted.

Moreover, premixing HTm4 with KAP abolished the KAP/HTm4 selective binding (data not shown). These in vitro data confirm that HTm4 and KAP interact directly and that the HTm4 C terminus is necessary and sufficient to mediate binding to KAP.

Example 3

KAP Phosphatase Activity is Enhanced in the Presence of HTm4

Figure 3:
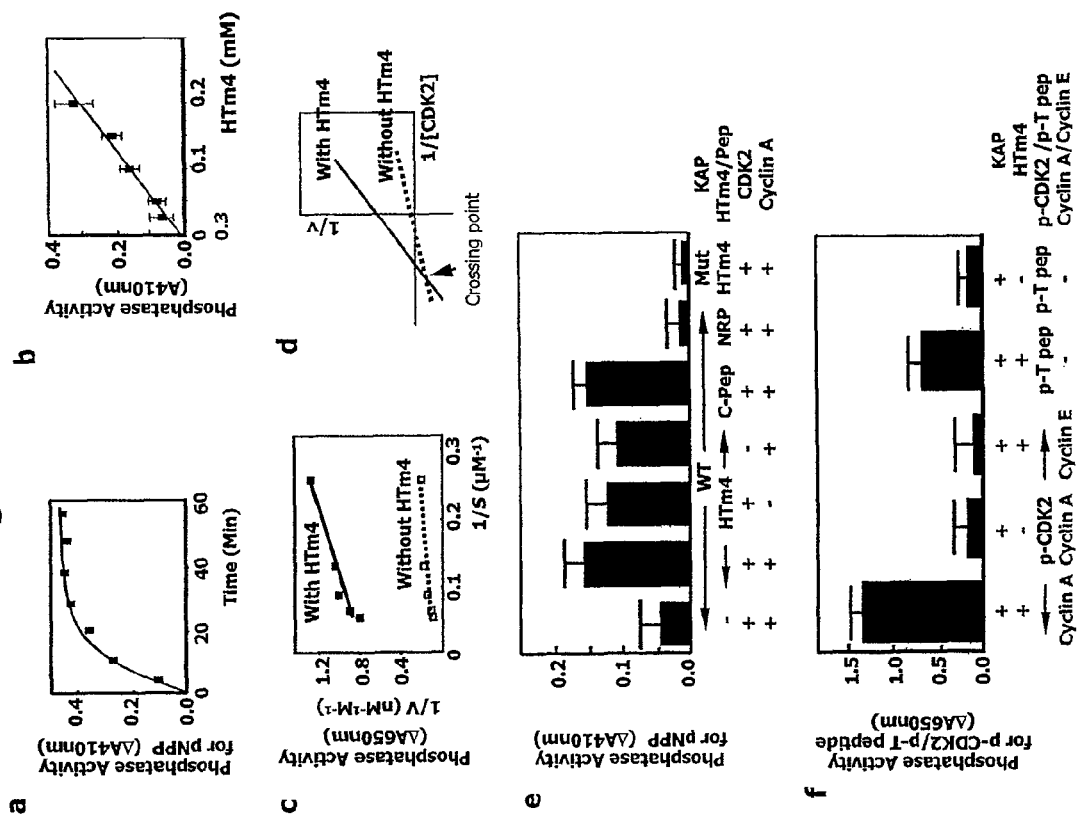
FIG. 3. HTm4 enhances KAP phosphatase activity. a, Graph sowing kinetics of wild-type KAP phosphatase activity. b, Graph showing the presence of HTm4 linearly increases KAP phosphatase activity. c, Lineweaver-Burk Plot showing KAP phosphatase activity. d, Dixon Plot showing KAP phosphatase activity. e, Graph showing effects of HTm4 on KAP phosphatase activity toward pNPP substrate. f, Graph showing effects of HTm4 on KAP phosphatase activity with phosphorylated cdk2 or cdk2-derived peptide as its substrate.

According to the invention, HTm4 is a direct binding partner for KAP. According to the invention, HTm4 may regulate the enzymatic activity of the KAP phosphatase. In the current experiment, KAP phosphatase activity was measured using pNPP as a generic substrate for KAP. In the presence of HTm4 and the cdk2.cyclin A-binding complex, a biphasic kinetic for KAP activity was observed. As shown in FIG. 3a, after the addition of pNPP substrate, an exponential phase (in the first 20 min) was followed by a plateau phase (after 30 min). The presence of HTm4 linearly increased the phosphatase activity of KAP ($y=1.45x+0.01$; $r2=0.98$) (FIG. 3b). Without HTm4, the Vmax and Km for KAP phosphatase activity were 1.30 nM/min and 2.68 µM, respectively (FIG. 3, c and d).

FIG. 3 shows HTm4 enhances KAP phosphatase activity. Kinetics of wild-type KAP phosphatase activity was demonstrated. 20 µl of reaction mixture containing 50 mM Tris-HCl, pH 7.5, 0.15 M NaCl, 2 mM DTT, 0.5 mM EDTA, 3 mM pNPP, 40 µM KAP, 4 µM cdk2.cyclin A, and 20 µM HTm4 was incubated at 30° C. for the indicated times. The reaction was halted by the addition of 0.1 M NaOH. The phosphatase activity in 5 µl of each sample was measured at 410 nm. The presence of HTm4 demonstrated a linearly increase in KAP phosphatase activity. KAP phosphatase activity was assessed in the presence of increasing amounts of HTm4 using pNPP as the KAP substrate. The reaction velocity was measured in the presence of 0.0025-20 µM HTm4. All reaction mixtures contained 40 µM KAP and 4 µM active cdk2.cyclin A. Reactions were repeated in triplicate. Their average values and standard deviations are shown. FIG. 3c shows a Lineweaver-Burk Plot. KAP phosphatase activity was assessed using the Ser/Thr Assay Kit 1 with different concentrations of active cdk2.cyclin A (from 4 to 20 µM) as the substrate in the presence or absence of 40 µM HTm4. $V_{max}$ and $K_m$ for the samples in the presence and absence of HTm4 are 17.5, 1.30 nM/min, and 8.33, 2.68 µM, respectively. FIG. 3d shows a Dixon Plot. KAP phosphatase activity was assessed using the Ser/Thr Assay Kit 1 with different concentrations of active cdk2.cyclin A (from 4 to 20 µM) as the substrate in the presence or absence of 40 µM HTm4.

However, when HTm4 was present, the Vmax of KAP phosphatase activity increased dramatically to 17.5 nM/min. A parallel increase in Km (to 8.33 µM) was also observed. Taken together, these data suggest that the presence of HTm4 directly affects the activity of the KAP phosphatase.

Example 4

KAP Dephosphorylation of Peptide or Protein Substrates

KAP dephosphorylation of phosphorylated proteins or peptide substrates was examined using the Ser/Thr Phosphatase Assay Kit 1 according to the manufacturer's instructions. Phosphorylated $Thr^{160}$ of cdk2 (p-cdk2) and K-R-pT-I-R-R peptides (SEQ ID NO:4) were used as substrates for the assay. Concentrations of KAP and HTm4 were both 20 µM; concentrations of p-cdk2 and peptide substrates (K-R-pT-I-

R-R, SEQ ID NO:4) were 10 and 25 μM, respectively. Reactions were performed in pNPP Ser/Thr Assay Buffer, containing 50 mM Tris-HCl, pH 7.0, and 100 μM CaCl$_2$. To examine the necessity of the HTm4 C-terminal region and to confirm the KAP phosphatase activity enhancement effect of HTm4, a peptide containing the last 22 amino acids of the HTm4 C terminus (CNANCCNSREEISSPPNSV SEQ ID NO:3) was synthesized. The phosphatase enhancement activity of the HTm4 C-terminal region was examined using the assay protocol described above. All assays were performed in triplicate, with the average values and standard deviations displayed on the plot.

Major factors affecting KAP phosphatase activity were further evaluated. KAP phosphatase activity is significantly enhanced in the presence of HTm4. When an inactive KAP mutant (C140S) is substituted for the wild-type KAP, the phosphatase activity is almost completely abolished. The inactive KAP mutant thus serves as a negative control. When HTm4 was absent or was replaced with a nonrelated peptide, KAP phosphatase activity was almost completely inhibited compared with control reactions containing wild-type KAP, HTm4, and cdk2.cyclin A complex (FIG. 3e).

FIG. 3e shows the effects of HTm4 on KAP phosphatase activity toward pNPP substrate. Activities of either wild-type (WT) or C140S inactive mutant KAP were examined in the different reaction mixtures, with or without 20 μM HTm4 (its C-terminal peptides/nonrelated peptides at 0.1 mM) or with 4 μM active cdk2.cyclin A (cdk2 monomer).

It is interesting to note that a cdk2.cyclin A complex, rather than either a monomeric cdk2 or cyclin A, was required for a stronger KAP phosphatase activity induced by HTm4. Additionally, the data suggest that KAP activity is optimal in the context of a multicomponent protein complex that contains its substrate, cdk2, and the HTm4 protein. The data demonstrate that wild-type KAP and HTm4 are essential for KAP phosphatase activity.

This experiment shows that the C-terminal region of HTm4, alone, was sufficient to mediate the HTm4-KAP interaction and to induce the KAP phosphatase activity. The same synthesized peptide containing the hypothesized KAP binding domain (CNANCCNSREEISSPPNSV SEQ ID NO:3) as described above was used. When introduced into an in vitro KAP activity assay, the HTm4 C-peptide showed a comparable enhancement effect on KAP phosphatase activity compared with HTm4 wild-type protein (FIG. 3e). These data both show that the C terminus of HTm4 mediates direct binding of HTm4 to KAP and show that the C terminus is the functional domain of HTm4 which regulates KAP activity.

Example 5

HTm4 Controls the Phosphatase Activity of KAP Toward its Physiological Substrates The data presented above demonstrate that HTm4 enhances the activity of the KAP phosphatase toward a generic substrate compound, pNPP. This experiment investigates whether HTm4 could also modify the activity of KAP toward its physiological substrates. The ability of KAP to dephosphorylate two of its substrates (FIG. 3f) was tested.

FIG. 3f shows the effects of HTm4 on KAP phosphatase activity with phosphorylated cdk2 or cdk2-derived peptide as its substrate. Phosphorylated threonine 160 from cdk2.cyclin A, active, and phosphopeptide (K-R-pT-I-R-R) were used as substrates to assess KAP activity. Assays were performed using the Ser/Thr Phosphatase Assay Kit 1. Concentrations of KAP and HTm4 were both 20 μM, and concentrations of p-cdk2 and peptide (K-R-pT-I-R-R) were 10 and 25 μM, respectively. Reactions were made in the pNPP Ser/Thr Assay Buffer, which contains 50 mM Tris-HCl, pH 7.0, and 100 μM CaCl$_2$. The reaction was allowed to proceed for 30 min at 30° C., and absorbance was measured at 650 nm.

First, cdk2 was examined with a phosphorylated Thr$^{160}$ (p-cdk2), which acts as a natural substrate for KAP. Then, a synthesized threonine phosphopeptide was used, K-R-pT-I-R-R (SEQ ID NO:4) (Upstate). The experiments showed that HTm4 increases the dephosphorylating activity of KAP toward phosphorylated cdk2 by more than 6-fold, when cdk2 is presented in the context of the cdk2.cyclin A complex. The experiments also demonstrated that HTm4 potentiates dephosphorylation of the synthesized phosphopeptide K-R-pT-I-R-R (SEQ ID NO:4). However, no KAP dephosphorylation activity could be detected if HTm4 was not presented. Interestingly, no dephosphorylation effect was observed when phosphorylated cdk2 was presented in the cdk2.cyclin A-binding complex. These data imply that the presence of HTm4 confers a substrate-specific enhancement of KAP phosphatase activity.

Example 6

Structural Change of KAP by Adding C-Peptide of HTm4

According to aspects of the invention, the observation that C-peptide of HTm4 protein enhanced KAP activity suggests that the binding of HTm4 C-peptide to the KAP molecule induced KAP conformational change. Also, the conformational changes of KAP in the presence or absence of the C-peptide were examined by using CD spectroscopy. The CD spectrum of a protein in the "near-ultraviolet" spectral region (250-350 nm) can be sensitive to certain aspects of tertiary structure. At these wavelengths the chromophores are the aromatic amino acids and disulfide bonds, and the CD signals they produce are sensitive to the overall tertiary structure of the protein. Signals in the region from 250 to 270 nm are attributable to phenylalanine residues, signals from 270 to 290 nm are attributable to tyrosine, and those from 280 to 300 nm are attributable to tryptophan. Disulfide bones give rise to broad weak signals throughout the near-ultraviolet spectrum.

Figure 4:
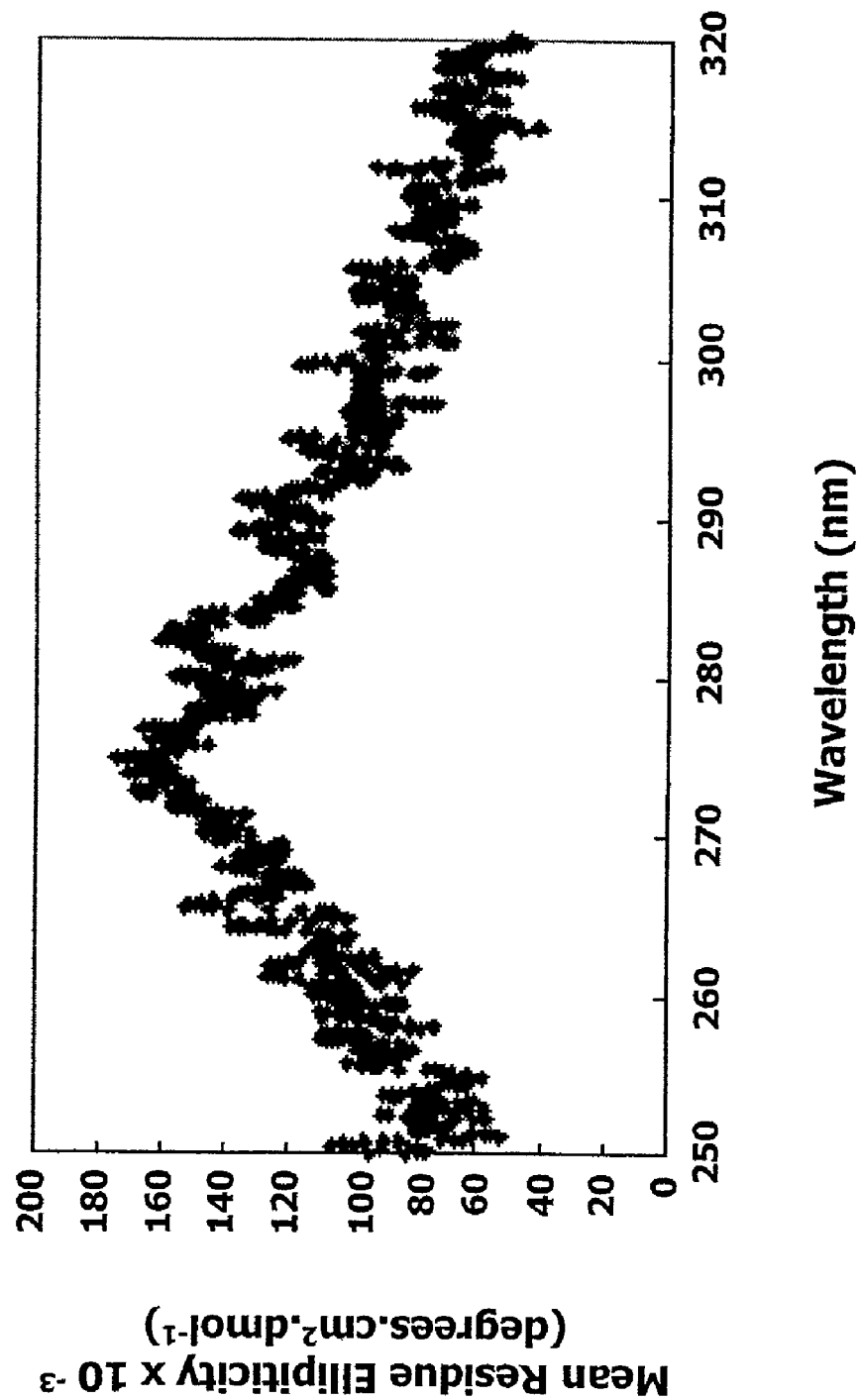
FIG. 4. Plot of KAP CD spectra change. Graph showing the difference in spectra measurements (ellipticity) recorded from 250 to 320 nm.

FIG. 4 shows a graph of KAP CD spectra change. Spectra measurements were recorded from 250 to 320 nm. The spectra change of KAP was measured by comparing two different KAP samples in the same solution (20 mM Tris-HCl, pH 7.2, 0.15 M NaCl). Sample A contains 5 μM KAP and an excess amount of HTm4 C-peptide (50 μM). Sample B was formulated as Sample A, with the exception of the HTm4 C-peptide. The difference in spectra was further converted to parameter (mean residue ellipticity) and plotted.

As shown in FIG. 4, a spectral change was found at 270-280 nm in the difference spectrum of KAP between sample A (with HTm4 C-peptide) and sample B (without C-peptide). The 270-290 nm difference spectrum demonstrated a conformational change in tyrosine when HTm4 C-peptide was added into KAP solution. Because HTm4 C-peptide has no tyrosine residues, this major change in the spectrum must be caused by conformational changes in the KAP tyrosine residues. Hence, this result demonstrated that HTm4 could cause direct conformational/tertiary structural change in KAP after its binding to KAP by the C terminus.

Example 7

HTm4 Dissociates Inhibitory Cyclin A from the cdk2.cyclin A-Binding Complex

The activity of cdk2 is controlled by its protein-protein interactions with KAP and cyclin A. The binding of KAP phosphatase to the cdk2.cyclin A complex dephosphorylates, and hence inactivates, cdk2. However, the binding of cyclin A inhibits the ability of KAP to dephosphorylate cdk2. Dissociation of cyclin A by HTm4 facilitates cdk2 dephosphorylation by KAP. Interestingly, HTm4 enhances the KAP dephosphorylation effect even on phosphorylated cdk2 that is presented in a complex with cyclin A. This result suggests that HTm4 may facilitate cdk2 inactivation by alleviating the inhibitory effect of cyclin A. The model suggests that HTm4 may dually regulate cdk2 activity, via KAP, and by physically excluding cyclin A from its inhibitory interaction with cdk2.

An affinity purification method was used to evaluate the cdk2-cyclin A interaction both with and without HTm4. His-tagged KAP protein was isolated using a $Ni^{2+}$ binding column. Without HTm4, cyclin A remained in the His-purified KAP.cdk2.cyclin A-binding complex (FIG. 5a). However, when purified HTm4 (after His tag cleavage) was added to the KAP.cdk2.cyclin A reaction mixture, cyclin A dissociated from the complex in a dose-dependent manner, and the remaining protein complex was found to contain only KAP cdk2.HTm4 (FIG. 5b).

Figure 5:
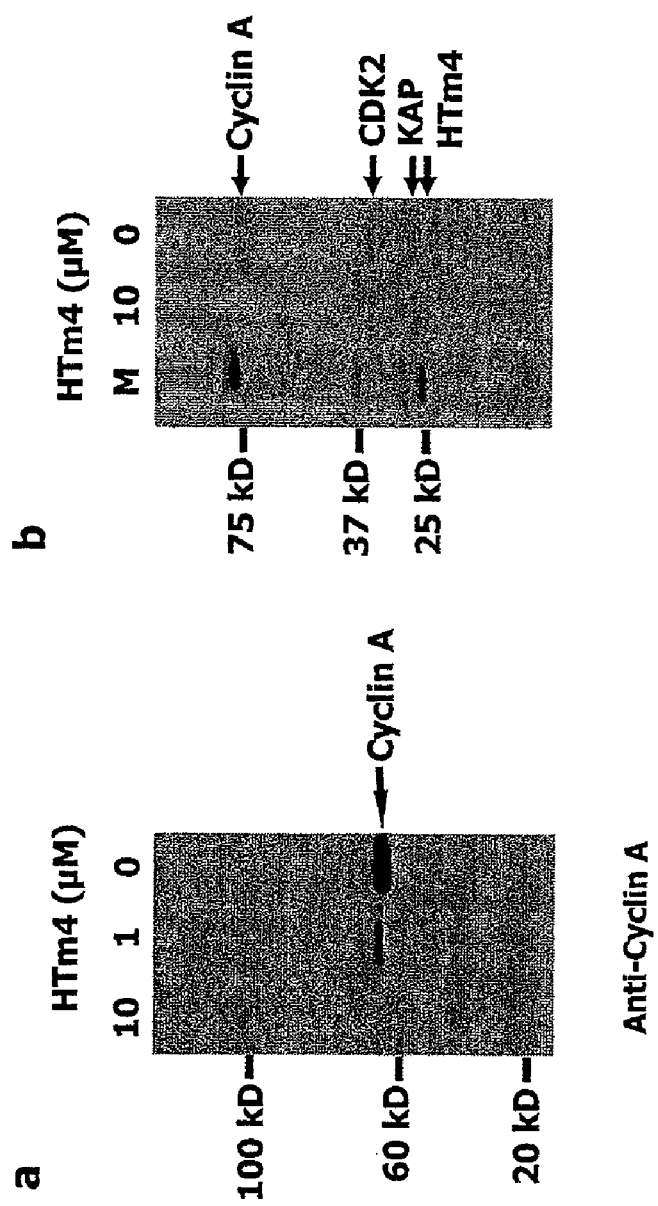
FIG. 5. Effects of formation of the cdk2-cyclin A complex in the presence or absence of HTm4. a, Western blot showing formation of the cdk2 cyclin A complex in the absence of HTm4. b, Western blot showing formation of cdk2 cyclin A complex in the presence of HTm4.

FIG. 5 shows the effects of formation of the cdk2.cyclin A complex in the presence or absence of HTm4. FIG. 5a shows formation of cdk2 cyclin A complex in the absence of HTm4. 10 µl of 10 µM cdk2.cyclin A and 10 µM His-tagged KAP were mixed, and the same amount of 10 µM HTm4 (left), 1 µM HTm4 (middle), or its buffer (right) was added to the mixture. After that, 5 µl of nickel magnet beads was added. Bound fractions were electrophoresed by SDS-PAGE and then detected by Western blotting with anti-cyclin A antibody as the primary antibody, and alkaline phosphatase-conjugated anti-rabbit IgG was used as the secondary antibody. The band of cyclin A is indicated with an arrow. FIG. 5b showed HTm4 released cyclin A. 10 µl of 10 µM cdk2.cyclin A and 10 µl of 10 µM His-tagged KAP were mixed in 20 mM Tris-HCl, pH 7.5, buffer containing 0.15 M NaCl, 1 mM 2-mercaptoethanol, and 0.1% Tween 20. After incubation at room temperature for 5 min, 10 µl of 10 µM HTm4 (without His tag) or its buffer was added to the mixture and allowed to incubate at room temperature for 5 mins. 5 µl of nickel magnet beads was added to each mixture. The bound fractions through His-tagged KAP were washed with the Tris buffer and boiled for SDS-PAGE. The gel was then silver stained. Bands of cyclin A, cdk2, and KAP are indicated with arrows.

These observations demonstrate that HTm4 inactivates cdk2 by activating KAP and by causing concomitant dissociation of cyclin A from cdk2. Together with the observation that HTm4 enhances KAP phosphatase activity, this suggests that HTm4 is positioned as a key regulator in the activation of KAP and for cdk2 activity.

Figure 6:
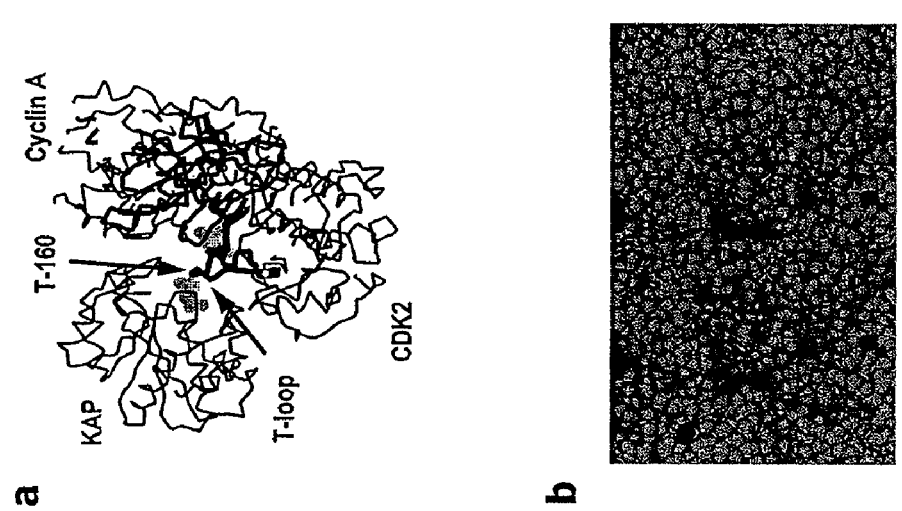
FIG. 6. KAP, cdk2, and cyclin A complex model. a, Model showing KAP, cdk2, and cyclin A interaction. b, Shows a stereo view of model complex cdk2 KAP and cyclin A.

FIG. 6 demonstrates a KAP, cdk2, and cyclin A complex model. FIG. 6a shows KAP, cdk2, and cyclin A interaction. Coordinates from cdk2.cyclin A and cdk2.KAP from the PDB were structurally aligned. A CPK trace was labeled. Both phosphorylated $Thr^{160}$ residues of the T-loops are shown on the CPK model. Extension of the T-loop is inhibited by an ionic interaction between $Arg^{157}$ of cdk and cyclin A $Glu^{268}$, as shown in FIG. 8a. b, stereo view of model complex cdk2 KAP and cyclin A. This view shows the reverse side of FIG. 8c, in a CPK model. The cyclin A molecule is viewed from the back of the cdk2.KAP complex.

Figure 7:
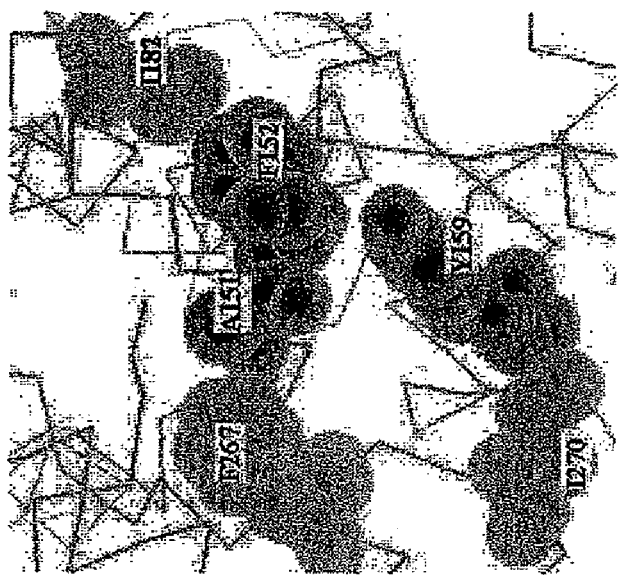
FIG. 7. Van der Waals interaction in KAP, cdk2, and cyclin A. a, Model showing Van der Waals interaction between the T-loop of cdk2 and cyclin A in the cdk2.cyclin A complex. b, Model showing the second interaction (between Phe$^{152}$ and Ile$^{182}$) is completely abolished by moving the T-loop.
Figure 7:
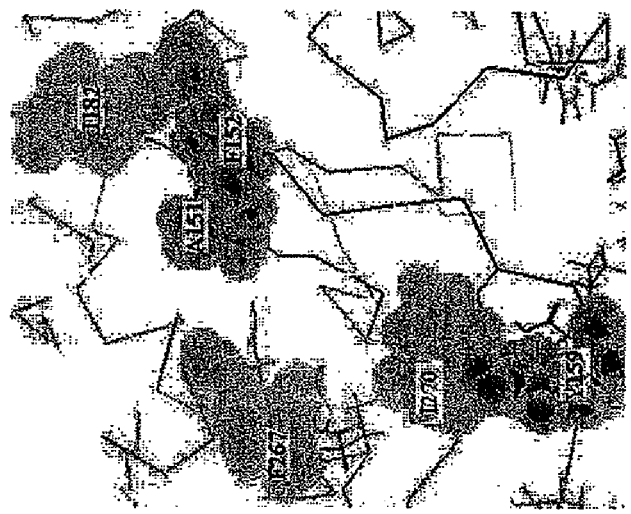

FIG. 7 shows Van der Waals interaction in KAP, cdk2, and cyclin A. FIG. 7a shows Van der Waals interaction between the T-loop of cdk2 and cyclin A in the cdk2.cyclin A complex. FIG. 7b shows the second interaction (between $Phe^{152}$ and $Ile^{182}$) is completely abolished by moving the T-loop.

Figure 8:
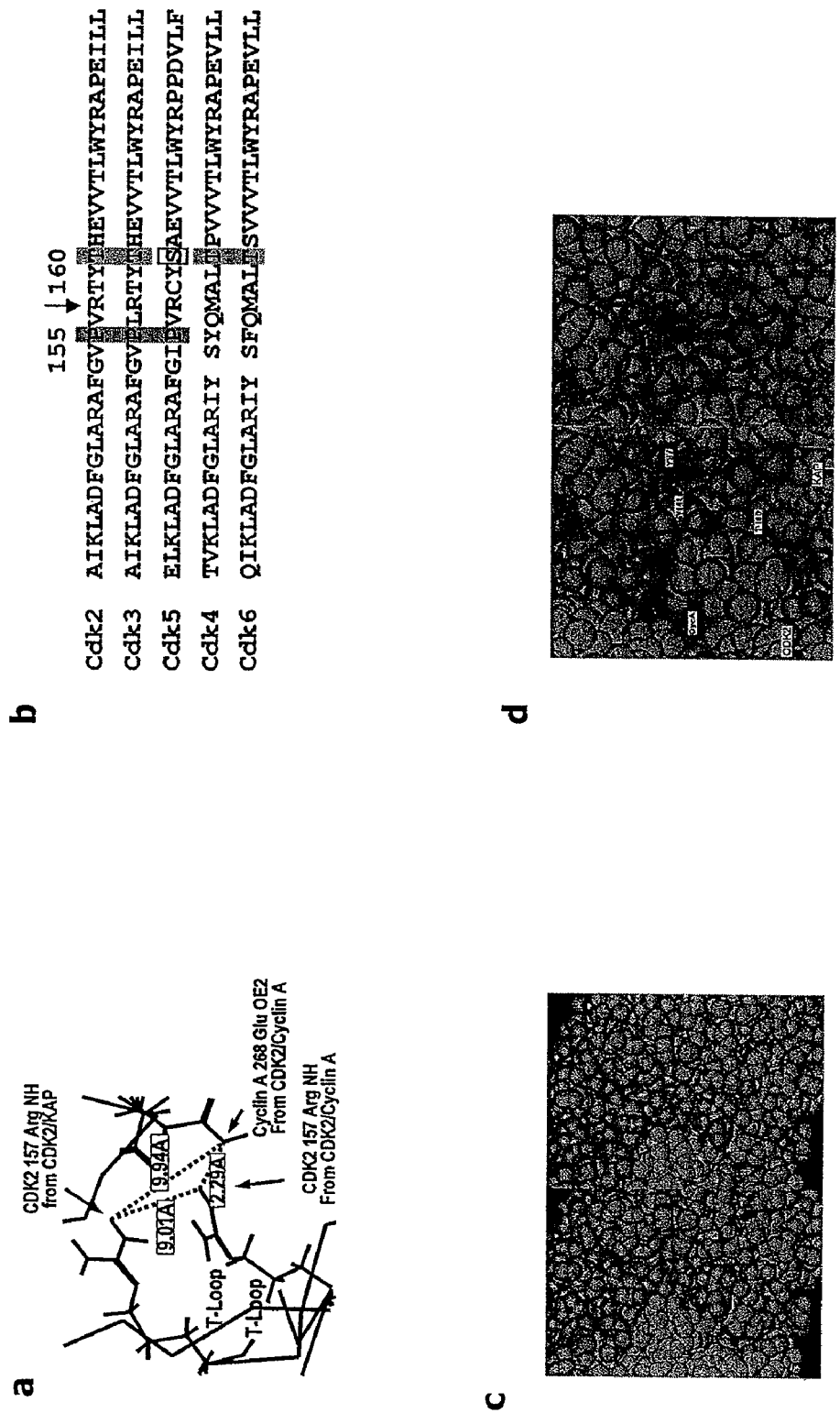
FIG. 8. KAP, cdk2, and cyclin A complex models. a, Model showing existence of ionic interaction between Arg157 of the T-loop of cdk2 and cyclin A Glu268 in the cdk2.cyclin A complex. b, Amino acid multialignment for cdks (Cdk2: SEQ ID NO: 7, Cdk3: SEQ ID NO: 8, Cdk5: SEQ ID NO: 9, Cdk4: SEQ ID NO: 10, Cdk6: SEQ ID NO: 11). c, Model showing a stereo view of the T-loop side in cdk2.cyclin A (1JST). d, Model showing a reverse side of KAP, cdk2 active site.

FIG. 8 shows KAP, cdk2, and cyclin A complex models. FIG. 8a shows the existence of ionic interaction between $Arg^{157}$ of the T-loop of cdk2 and cyclin A $Glu^{268}$ in the cdk2.cyclin A complex but not in the cdk2.KAP complex. The calculated distances are based on coordinates of cdk2.cyclin A in PDB and the model in cdk2.KAP. FIG. 8b shows amino acid multialignment for cdks. The numbers on the top of the alignment are from the amino acid sequence of cdk2. Conserved $Arg^{157}$ is indicated with an arrow. FIG. 8c shows the stereo view of the T-loop side in cdk2.cyclin A (1JST). $Pro^{155}$ of cdk2 is shown in the deep concave. The Pro residue seems not to be accessible by an isomerase. FIG. 8d shows a view of a reverse side of FIG. 6b (KAP, cdk2 active site) and is also shown by CPK model. $Thr^{160}$ of cdk2 and cyclin A are shown on the back side of the cdk2.KAP complex. A broad concave that HTm4 C-terminal domain would bind can stereographically be seen. Tyrosine residues 87 and 141 of KAP represent the candidate conformational change sites after the HTm4-C-terminal binding shown by CD difference spectrum (FIG. 4).

Figure 9:
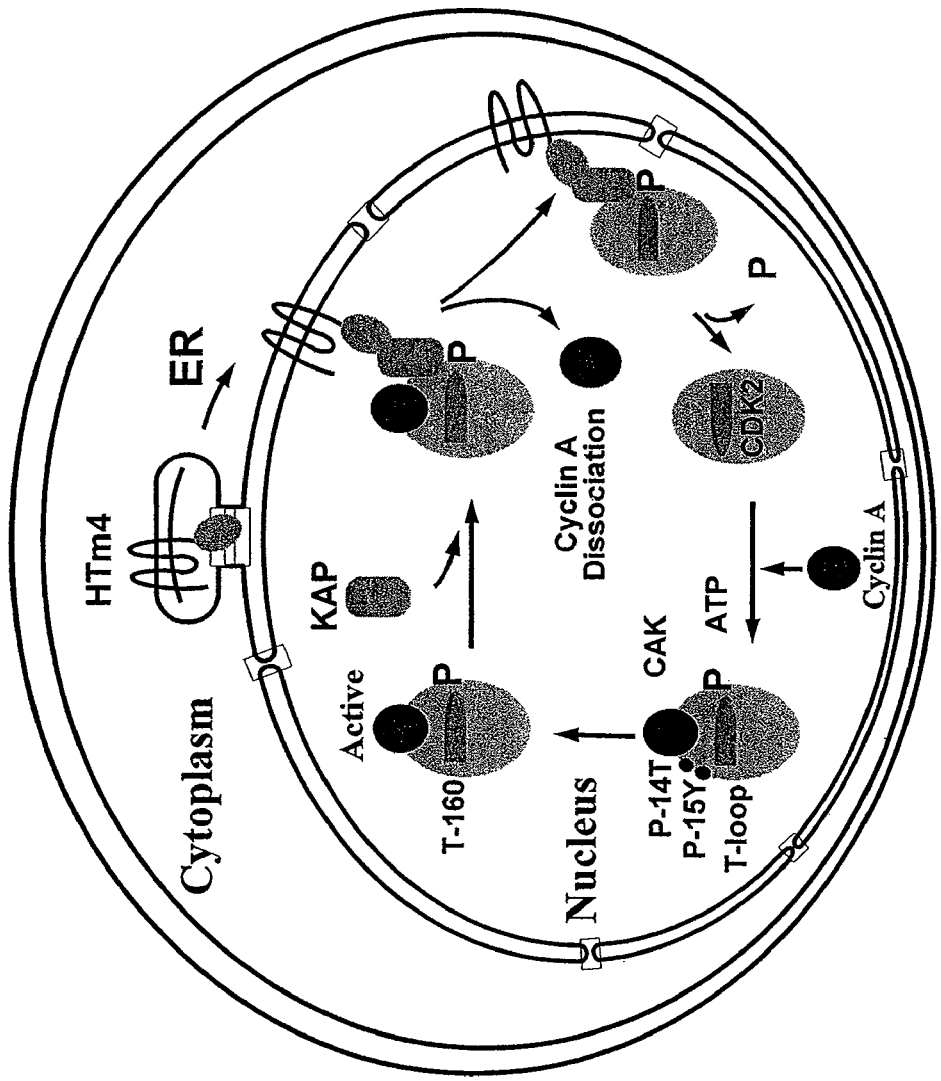
FIG. 9. Schematic showing proposed mechanism of action for HTm4.

FIG. 9 shows a proposed mechanism of action for HTm4. Cdk2 is activated by cyclin A binding and $Thr^{160}$ phosphorylation. While not being limited to any hypothesis or mechanism, the active form of cdk2 may bind KAP and HTm4 and may hence be tethered to the nuclear membrane. The active cdk2.cyclin A will not be inactivated by KAP dephosphorylation at $Thr^{160}$ until cyclin A is dissociated by HTm4. Thus HTm4 plays a key role in cell cycle regulation via the HTm4-KAP-cdk2 cascade.

Example 8

Mechanism for HTm4-Induced Dissociation of Cyclin A from Cdk2 Cyclin A

In silico modeling was used to probe the potential nature of the HTm4 regulatory interaction that promotes KAP phosphatase activity and potentially leads to the exclusion of cyclin A. According to aspects of the invention, KAP undergoes conformational changes following allosteric binding to the HTm4 C-terminal domain and that these conformational changes may subsequently facilitate the interaction between the KAP substrate and its active site. To examine this hypothetical model, a steric structure model was produced using the coordinates of cdk2.cyclin A (1JST) (21) and cdk.KAP (1FQ1) (20) from the Protein Data Bank (PDB). These structures were overlapped utilizing Homology in Insight II software (MSI). The resulting model complex is shown in FIG. 6a. Both cdk structures significantly overlap, and the overall RMS deviation is 0.92 Å, with the exception of the T-loop region. In this region, marked differences in cdk structure can be noted, depending on whether coordinates are derived from the cdk2.cyclin A or the cdk2.KAP complex. There is a deep concave face, as shown in FIG. 6b. According to aspects of the invention, the concave face may form a potential docking site for the HTm4 C terminus. On the reverse side of the interface, phosphothreonine 160 of cdk2 can be inserted into the entrance of the active site of KAP in the absence of cyclin A, whereas a small molecule of substrate such as pNPP may still be able to enter the entrance even in the presence of cyclin A. This finding may explain why KAP activity toward pNPP is enhanced at moderate levels in the presence of the cdk2.cyclin A complex.

Mode of Structural Change of the Cdk2 T-Loop in the Absence and Presence of HTm4

The T-loop is a conserved segment in cdks, which plays an important role in cdk activation. In the cdk2.cyclin A complex, phosphorylation is associated with the mobility of the T-loop (Taniguchi, T., Endo, H., Chikatsu, N., Uchimaru, K., Asano, S., Fujita, T., Nakahata, T., and Motokura, T. (1999) *Blood* 93, 4167-4178). However, viral cyclins (K-, H-cyclins) can still activate cdk6 without $Thr^{177}$ phosphorylation, which corresponds to $Thr^{160}$ phosphorylation in cdk2. The degree of interaction between the T-loop of cdk6 and V-cyclin is shown to be critical because the interaction area between cdk6 and V-cyclin was 20% larger than that of cdk2 and cyclin A (Gyuris, J., Golemis, E., Chertkov, H., and Brent, R. (1993) *Cell* 75, 791-803). This increased interaction is contributed mainly by the T-loop of cdk6. Hence, the movement of the T-loop is critical for cdk activation.

In the cdk2.cyclin A activation model, van der Waals interactions exists between $Ala^{151}$, $Phe^{152}$, and $Tyr^{159}$ of the cdk2 T-loop and $Phe^{267}$, $Ile^{182}$, and $Ile^{270}$ of cyclin A (FIG. 7a) (Morgan, D. O. (1997) *Annu. Rev. Cell Dev. Biol.* 13, 261-291). However, in the KAP.cdk2.cyclin A complex model, the second cdk2-cyclin A interaction ($Phe^{152}$-$Ile^{182}$) is completely abolished if the T-loop is moved because of the interaction of KAP (FIG. 7b). This result demonstrates that binding of KAP to cdk2 weakens the interactions between cdk2 and cyclin A. Moreover, it is reported that interactions between the T-loop of cdk2 and KAP comprise van der Waals interactions between residues $Tyr^{141}$ and $Phe^{53}$ of KAP with residue His161 of cdk2.

Besides the van der Waals interaction between the T-loop of cdk2 and cyclin A, a specific ionic interaction also exists between the —NH at $Arg^{157}$ of cdk2 and the —OH of $Glu^{268}$ of cyclin A in cdk2.cyclin A complex. This interaction disappears when the cyclin A molecule is dissociated, as seen in the cdk2.KAP complex (FIG. 8a). Thus, the extension of the T-loop in cdk2.cyclin A is inhibited by this ionic interaction.

In PDB models, more than 20 sets of coordinates are deposited for cdk2, both with and without cyclin A or its inhibitors. Each structure of the T-loop was investigated and dihedral angles were measured between $Val^{154}$ and $Pro^{155}$, which are conserved in several cdks. FIG. 8b shows amino acid multialignments for several cdks. When cdk2 is associated with cyclin A, the T-loop is shortened with cis-Pro at position 155. Conversely, without cyclin A, the loop is extended with trans-Pro (Table I). When bound to KAP (without cyclin A), the T-loop of cdk2 shows extension in the trans form. According to the predicted crystal structure of cdk2.cyclin A, this cis-trans conversion at $Pro^{155}$ is thought to occur automatically because the residue $Pro^{155}$ would no longer be accessible to an isomerase (FIG. 8c).

TABLE I

ωAngles between $Val^{154}$ and $Pro^{155}$ in the T-loop of cdk2 from the PDB Coordinates from PDB of cdk2 with or without cyclin A or KAP were down-loaded from PDB, and angles were measured.

| PDB code | ω (Degree) | TL[a] | Cyclin | A/KAP |
|---|---|---|---|---|
| 1JSU | -13.76 | cis | E | (+)/(−) |
| 1JST | 5.87 | cis | E | (+)/(−) |

TABLE I-continued

ωAngles between $Val^{154}$ and $Pro^{155}$ in the T-loop of cdk2 from the PDB Coordinates from PDB of cdk2 with or without cyclin A or KAP were down-loaded from PDB, and angles were measured.

| PDB code | ω (Degree) | TL[a] | Cyclin | A/KAP |
|---|---|---|---|---|
| 1E9H | 0.06 | cis | E | (+)/(−) |
| 1H28 | 6.61 | cis | E | (+)/(−) |
| 1QMZ | 36.92 | cis | E | (+)/(−) |
| 1FQ1 | 175.31 | trans | S | (−)/(+) |
| 1HCK | 170.27 | trans | S | (−)/(−) |
| 1PF8 | 166.29 | trans | S | (−)/(−) |
| 1PW2 | 177.23 | trans | S | (−)/(−) |

[a]TL, T-loop; E, extended; S, shortened.

When cyclin A dissociates from cdk2, the T-loop will extend through cis-trans conversion at the $Pro^{155}$ residue, and phosphothreonine 160 can then be inserted into the active site of KAP. Thus, the susceptibility of phosphothreonine 160 to KAP phosphatase occurs in response to HTm4 binding to KAP. $Pro^{155}$ commonly exists in cdk3, cdk5, but not cdk4, cdk5 as shown in FIG. 8b, whereas its counterpart residue $Glu^{258}$ is conserved in cyclins A, B, E, and C but not in cyclin D. This disparity suggests that mechanisms for cdk inactivation by KAP may differ between cdk species and hence between different phases of the cell cycle.

Binding Site of HTm4

In FIG. 8d, the close allosteric position is shown between $Thr^{160}$ of cdk2 and $Tyr^{84}$, $Tyr^{141}$ of KAP, which suggests that the concave face of KAP accepts the HTm4 C terminus via the $Tyr^{141}$ residue of KAP. Immediately following HTm4 binding, the conformational change of the $Tyr^{141}$ residue of (FIG. 4) will weaken the van der Waals interaction between cdk2 and cyclin A and then affect continuously alongside T-loop (from residues 142 to 165) involving $Ala^{151}$, $Phe^{152}$, and $Tyr^{159}$. This HTm4 binding eventually dissociates cyclin A from cdk2, thereby inducing a structural change of cdk2. At the reverse side of the interface, phosphothreonine 160 of cdk2 is inserted into the entrance of the active site of KAP, after cyclin A is released.

Model of Action Mechanism for HTm4

HTm4 has four transmembrane domains. Topologically, this structure provides two tails that are available for protein-protein interactions. HTm4 localizes to the nuclear membrane. According to aspects of the invention, the tails of HTm4 may extend into the nuclear lumen and tether the KAP.cdk2.cyclin A complex (FIG. 9). The interaction between HTm4 and the KAP.cdk2.cyclin A complex is likely reversible and may occur only at certain stages in the cell cycle. HTm4 significantly affects the activity of KAP, cdk2, and cyclin A. HTm4 also regulates cdk2 activity in a dual fashion, by concurrently activating KAP activity and facilitating the accessibility of $Thr^{160}$ to KAP by causing dissociation of inhibitory cyclin A (FIG. 9). Accordingly, HTm4 may regulate the cell cycle in hematopoietic cells and other cells through its ability to control cdk2 status.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All publications, patents and sequence database entries mentioned herein, including those items listed below, are hereby incorporated by reference in their entirety as if each individual publication or patent was specifically and individually indicated to be incorporated by reference. The disclosures of U.S. Pat. Nos. 6,153,403; 5,972,688; 5,767,073; 5,705,615; 5,585,478; and 5,552,312 are incorporated herein by reference in their entirety. In case of conflict, the present application, including any definitions herein, will control.

What is claimed is:

1. A method of destabilizing a cdk2/cyclin A complex, the method comprising:
   contacting a cdk2/cyclin A complex with a polypeptide comprising the amino acid sequence of SEQ ID NO: 3 in an amount effective to destabilize the cdk2/cyclin A complex.

2. The method of claim 1, wherein the polypeptide consists of the amino acid sequence of SEQ ID NO: 3.

3. A method of synchronizing cell cycles, the method comprising:
   contacting a cell with an isolated C-terminal fragment of HTm4 comprising the amino acid sequence of SEQ ID NO: 3 in an amount effective to destabilize a cdk2/cyclin A complex, or contacting a cell with an antibody or antibody fragment that specifically binds HTm4 in an amount effective to stabilize a cdk2/cyclin A complex.

4. A composition comprising an isolated HTm4 C-terminal fragment, wherein the C-terminal fragment consists of the amino acid sequence of SEQ ID NO: 3.

5. A pharmaceutical preparation comprising the composition of claim 4.

6. The method of claim 1, wherein the cdk2/cyclin A complex is contacted with the polypeptide in the presence of KAP.

7. The method of claim 2, wherein the cdk2/cyclin A complex is contacted with the polypeptide in the presence of KAP.

8. The method of claim 3, wherein the isolated C-terminal fragment of HTm4 consists of the amino acid sequence of SEQ ID NO: 3.

* * * * *